United States Patent [19]
Kirby et al.

[11] Patent Number: 5,670,949
[45] Date of Patent: *Sep. 23, 1997

[54] CARBON MONOXIDE/HYDROCARBON THIN FILM SENSOR

[75] Inventors: Kevin W. Kirby, Calabasas Hills; Hiroshi Kimura, Northridge; M. Duchesne Courtney, Mission Hills, all of Calif.

[73] Assignee: Hughes Aircraft Company, Los Angeles, Calif.

[*] Notice: The term of this patent shall not extend beyond the expiration date of Pat. No. 5,252,949.

[21] Appl. No.: 173,306

[22] Filed: Dec. 23, 1993

[51] Int. Cl.$^6$ .................................. G08B 17/10
[52] U.S. Cl. .................... 340/632; 73/23.31; 340/633
[58] Field of Search ................ 340/632–634, 340/439; 324/693; 73/23.31, 23.32, 118.1, 118.2

[56] References Cited

U.S. PATENT DOCUMENTS 4,968,656  11/1990  Fukuda et al. ...................... 502/244
5,157,921  10/1992  Ito et al. .......................... 73/118.1 X
5,252,949  10/1993  Kirby et al. ....................... 340/632

FOREIGN PATENT DOCUMENTS 1076948  4/1986  Japan ................ 73/23.31
1150849  6/1986  Japan ................ 73/23.31
2021259  1/1990  Japan ................ 73/23.31
2149122  6/1985  United Kingdom ...... 324/693

*Primary Examiner*—Thomas Mullen
*Attorney, Agent, or Firm*—V. D. Duraiswamy; W. K. Denson-Low

[57] ABSTRACT

A ceramic sensor comprising a thin film of $Cu_xMn_{3-x}O_4$ is provided that quantitatively measures the partial pressure of CO and hydrocarbon gases in a flowing system. The sensor is specific to both CO and hydrocarbon gases and is negligibly affected by the presence of the common automobile exhaust vapors NO and $H_2O$, within the operational temperature range from about 250° to 450° C. The CO/hydrocarbon sensor of the invention has other applications, such as monitoring CO and hydrocarbon levels in laboratories, mines, and industrial smoke stacks, and may be used in environments up to about 700° C.

20 Claims, 6 Drawing Sheets

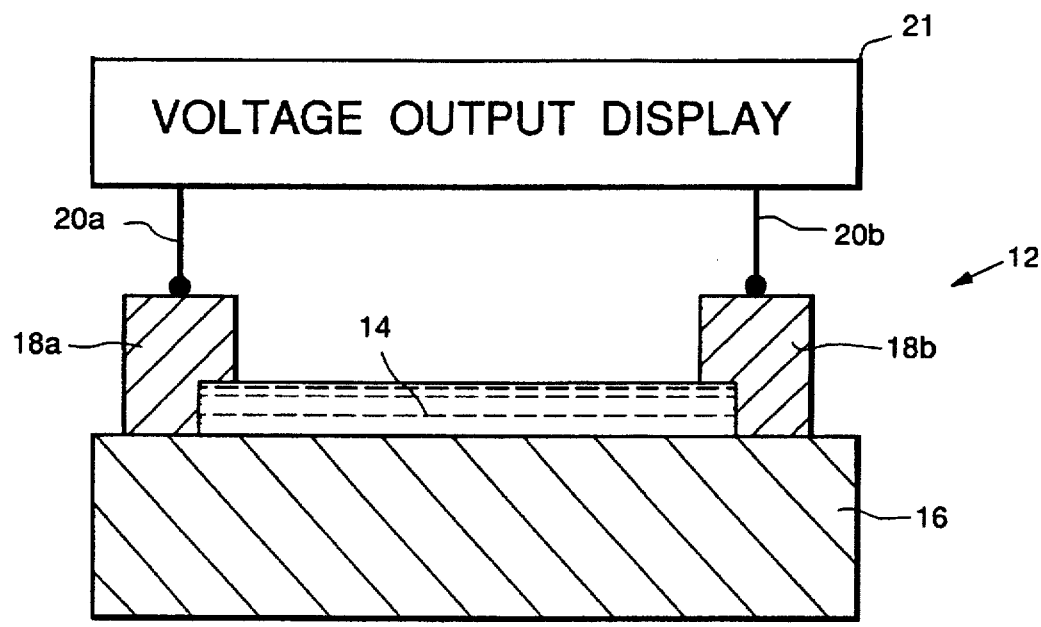
FIG. 2.
FIG. 3.
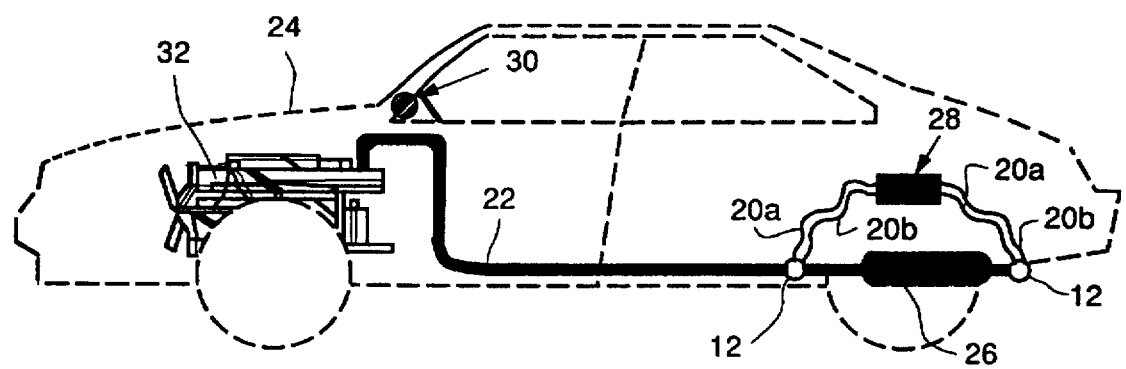

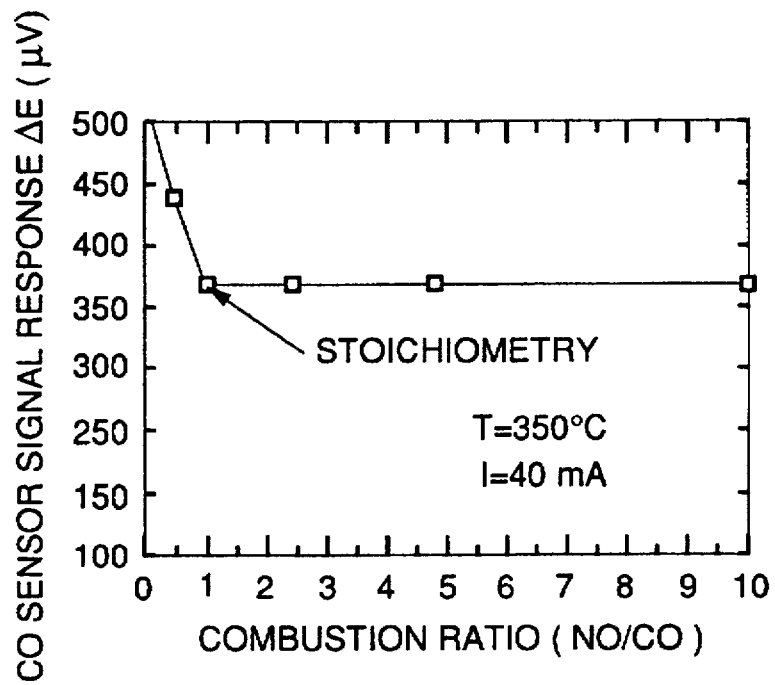
FIG. 10.
FIG. 11.
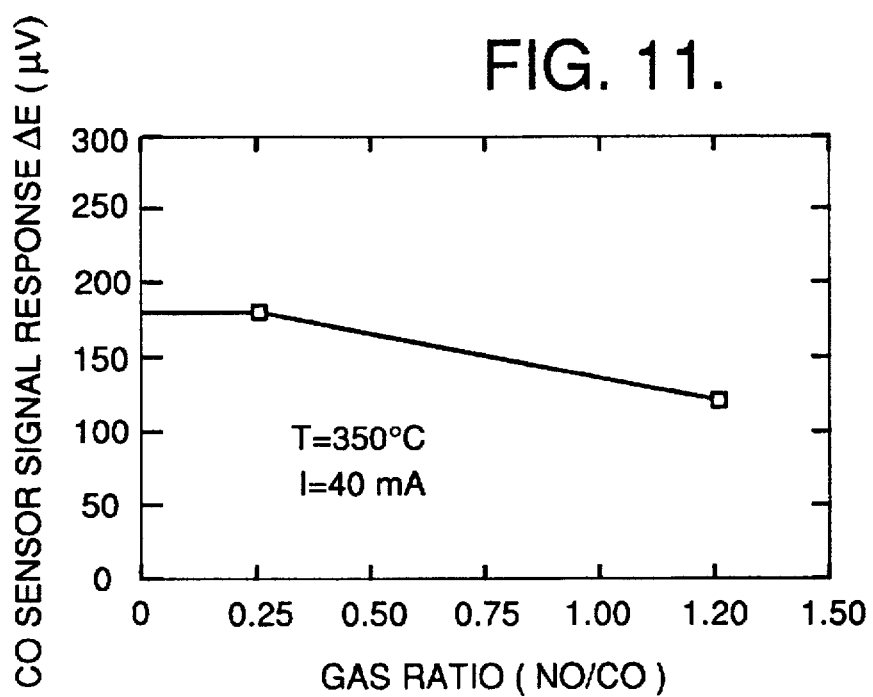

CARBON MONOXIDE/HYDROCARBON THIN FILM SENSOR

CROSS-REFERENCE TO RELATED APPLICATION

The present application is related application of application Ser. No. 07/751,029, filed Aug. 28, 1991 now U.S. Pat. No. 5,252,949.

BACKGROUND OF THE INVENTION

1. Field of the Invention

The present invention relates to detection of automobile exhausts, and, more particularly, to the detection of carbon monoxide and hydrocarbon gases in the presence of other gases.

2. Description of Related Art

A sensor for carbon monoxide (CO) and hydrocarbon (HC) gases has immediate application to automobiles for monitoring catalytic converter efficiency. Sensors placed before and after the catalytic converter would be able to quantitatively monitor the oxidation efficiency of environmentally harmful CO and HCs by the converter. Another automobile application includes real-time control of engine processes via a feedback loop of exhaust composition from a strategically located sensor.

Semiconductive metal oxides have been used as CO and hydrocarbon sensors. Two major problems are encountered, however. The first is a non-linearity in the signal response when the mixture of oxidizable gas and oxygen reaches a stoichiometric ratio for combustion. For the case of CO, this occurs when the $CO/O_2$ ratio equals 2:1 in the following reaction:

(1)

When this ratio is attained, the signal can change by over an order of magnitude, and the calibration of sensor is therefore lost.

The second problem encountered with metal oxide sensors is a lack of detection specificity with respect to an individual gas in a gas mixture. This can be a particular problem in the case of automobile exhaust, where signal interference can arise from the presence of oxides of nitrogen ($NO_x$), $H_2O$ vapor, and other hydrocarbon gases resulting from fuel combustion. For example, presently-employed exhaust sensors use $SnO_2$, which is deleteriously affected by the presence of $H_2O$ and $NO_x$. Signal fluctuations with changing ambient oxygen partial pressure, $P(O_2)$, during measurement have also limited the use of these sensors for automobile applications.

Thus, there is a need for a CO and HC sensor that is substantially free of the problems of the prior art sensors.

SUMMARY OF THE INVENTION

In accordance with the invention, a thin film sensor is provided that quantitatively measures the partial pressure of CO and HC gases in a flowing system. The sensor is specific to both CO and HC gases and is negligibly affected by the presence of the common automobile exhaust vapors $NO_x$ and $H_2O$, within the operational temperature range from about 250° to 450° C.

The sensor of the invention comprises a defect copper manganese oxide, $Cu_xMn_{3-x}O_4$, having the spinel structure, where $0<x\leq1.5$. While one sensor might be used in a particular application, a pair of sensors is desirably employed in connection with the monitoring of CO and HC gases in automobile exhaust, one placed before the catalytic converter and one placed after, to determine the efficiency of the catalytic converter.

The sensor of the invention comprises a thin film of the copper manganese oxide, supported on a substrate, to which metal contact is made so as to measure any change in surface resistance during exposure to CO and HC gases in the exhaust gas stream. Such a change in resistance is a measure of the quantity of CO and HC gases.

As indicated above, the present invention is directed to a thin-film metal-oxide sensor sensitive to carbon monoxide and hydrocarbons; however, the sensor is insignificantly affected by $H_2O$ and $NO_x$. This behavior is especially suitable for automobile exhaust evaluation. The sensor of the invention also has a calibrated signal response proportional to the concentration of CO or HC in the ambient gaseous surroundings. Other gas species simultaneously present do not significantly interfere or modify the sensor signal. The sensor does not appear to be sensitive to fluctuations in the ambient oxygen partial pressure, or $P(O_2)$, as long as the $P(O_2)$ is greater than the combined partial pressures of the CO and hydrocarbons. The sensor signal is generated by a conductivity change in the material when in the presence of either CO or HC. This conductivity change is easily measured by determining the change in voltage necessary to drive a constant current through the sensor.

The sensor of the present invention permits measurement of the concentration of CO and HC in automobile exhaust environments to determine if the catalytic converter is functioning properly, to determine the total output of these two gases over a specified time period, and to feed information back to the automobile for adjustments in combustion ratios for improved performance.

BRIEF DESCRIPTION OF THE DRAWINGS

FIG. 2 is a cross-sectional view of the CO sensor of the invention;

FIG. 3 is a schematic diagram depicting one use of the CO sensor of the invention;

FIG. 10, on coordinates of CO sensor signal response (in μV) and combustion ratio (of O:CO), is a plot showing the bulk sensor signal response to 4% CO in nitrogen with changing oxygen concentration;

FIG. 11, on coordinates of CO sensor signal response (in μV) and NO/CO gas ratio, is a plot depicting the bulk sensor response to 4% CO with increasing NO gas concentration;

DESCRIPTION OF THE PREFERRED EMBODIMENTS

Figure 1A:
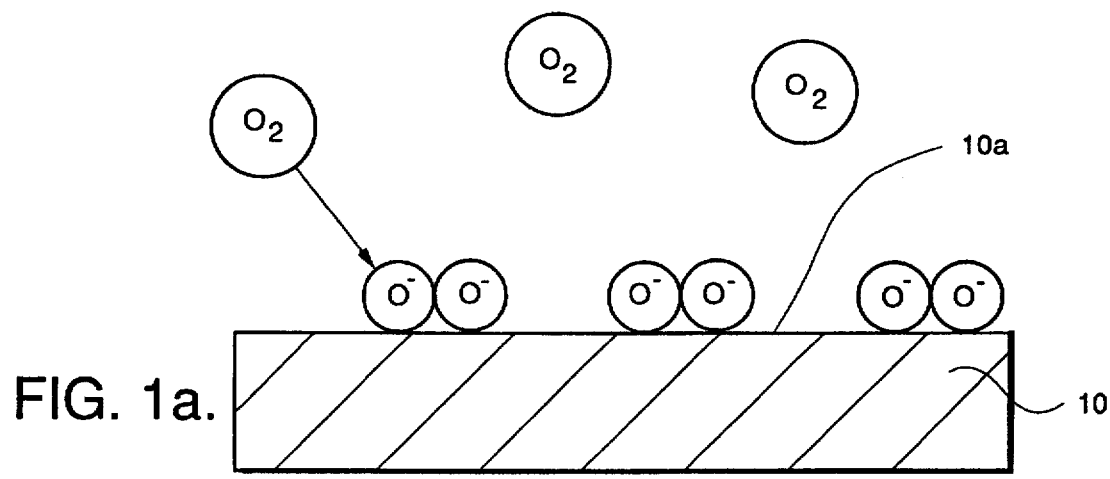
FIGS. 1a–c are a schematic representation of what is believed to be occurring on the surface of the CO sensor of the invention.

A thin film sensor has been developed that quantitatively measures the partial pressure of CO and HC gases in a flowing system. The sensor is specific to CO and HC gases and is negligibly affected by the presence of the common automobile exhaust vapors $NO_x$ and $H_2O$ within the operational temperature range of about 250° to 450° C. and within the compositional range encountered in automobile exhaust.

The sensor of the invention has been made in thin film form easily and inexpensively from a metallo-organic deposition (MOD) process. The MOD process consists of dissolving together organic salts of the metal constituents into a solution which is then deposited onto the surface of an appropriate substrate and is described more fully below. Examples of materials employed as appropriate substrates include insulating materials, such as oxides (alumina, magnesia, zirconia, etc). Deposition techniques include spray, dip, or spin coating of the solution. The deposited solution is then dried and heated at temperatures of at least about 800° C. to form the crystalline ceramic oxide. Films with thicknesses up to 1 μm and greater may be fabricated.

A sensor test structure includes a film produced by this or other deposition technology on a suitable substrate, and a 2-point or interdigitated array of metal electrodes contact the film surface. Metal electrodes such as gold have been evaporated onto film surfaces, with the desired pattern easily produced by masking. Other techniques include screen printing platinum electrodes onto the substrate before deposition of the film. Leads from the metal electrode connect to current generating and resistance measuring circuitry to provide electrical evaluation of the sensor.

The thin film sensor of the invention has the ability to determine levels of CO and HC gases emanating from automobile combustion, without the detrimental effects encountered from other combustion by-products, as indicated above. Since the sensor of the invention comprises a metal oxide, it is able to operate at relatively high temperatures with minimum degradation of integrity.

The sensor of the invention employs copper-manganese oxide, which has a spinel structure and is easily prepared in thin film form, as described above. The resulting material is described by the formula $Cu_xMn_{3-x}O_4$, where x ranges from a value greater than zero to a value not exceeding 1.5; that is, $0<x\leq 1.5$. This compound is a defect version of the parent compound, $CuMn_2O_4$, with the Cu cations occupying the octahedral Mn sites in the spinel structure. This type of behavior is well-documented for a variety of spinel-type oxides, and contributes to the semiconductive behavior observed in this material and ultimately to the material's sensor capability.

The principle of operation relies on the chemisorption and subsequent reaction of gaseous species on the sensor surface. For the case of detecting CO in a gaseous mixture having a partial pressure of oxygen [$P(O_2)$ finite], both CO and $O_2$ molecules are attracted to the sensor surface and undergo chemisorption. Reaction of these molecules at the surface via Eqn. 1 with subsequent desorption of the resulting $CO_2$ molecule establishes an equilibrium at the surface with respect to the concentration of chemisorbed molecules. Assuming that $CO_2$ formation (Eqn. 1) proceeds more slowly than the chemisorption process, then the concentration of CO and $O_2$ molecules on the surface becomes a function of their respective partial pressures in the gas mixture. Molecules of CO are reducing and tend to donate electrons during chemisorption, while $O_2$ molecules ionize to $O^{n-}$, thereby removing electrons from the surface. It is this balance that dictates the free carrier population and mobility on the sensor surface and therefore the surface resistance. As this balance changes due to the partial pressure change of CO in the gas mixture, there is a corresponding change in the surface resistance of the sensor, providing the basis for a signal response.

Hydrocarbon species are also chemisorbed in a similar manner on the sensor surface and react with surface oxygen to produce the same effect, via the reaction

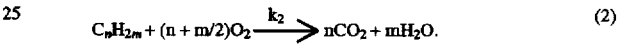

$$C_nH_{2m} + (n+m/2)O_2 \xrightarrow{k_2} nCO_2 + mH_2O. \quad (2)$$

Figure 1B:
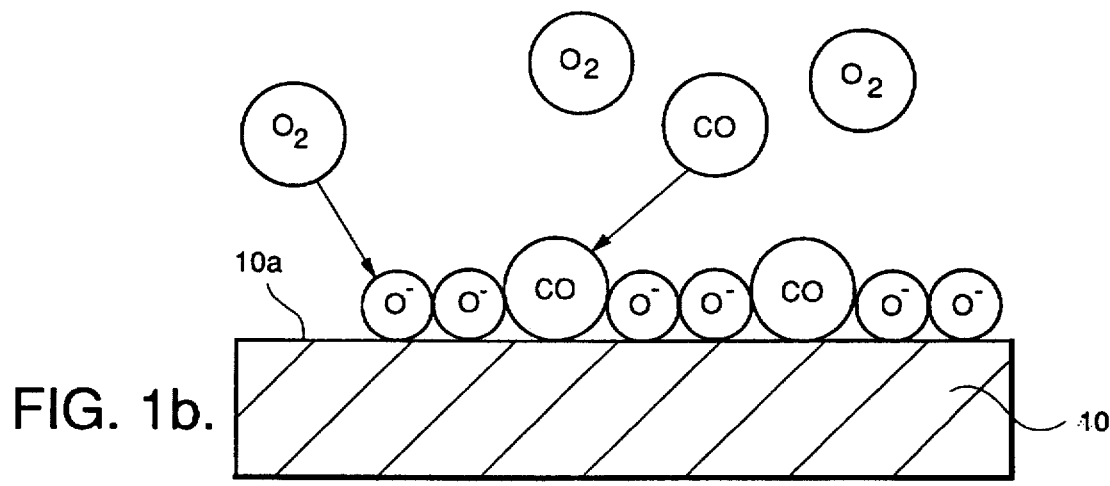
Figure 1C:
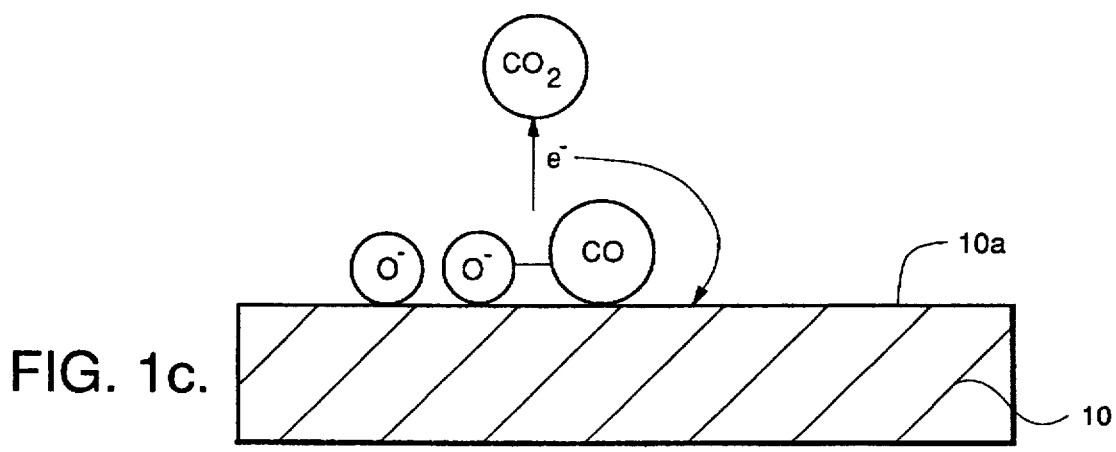

Without subscribing to any particular theory, a model is presented in FIGS. 1a–c, which illustrates material changes in the sensor due to the presence of carbon monoxide and is the basis for the quantitative detection of this gas. As shown in FIG. 1a, in the presence of a partial pressure of oxygen [$P(O_2)$ finite], a surface 10a of a sample 10 attracts oxygen in a chemisorption process, forming oxygen anions ($O^{n-}$). FIG. 1a depicts this process, showing $O^-$ anions on the sample surface 10a. The corresponding equation relating to chemisorption is given by

$$2e^- + O_2 \xrightarrow{k_3} 2O^-. \quad (3)$$

It will be observed that for this process to occur, electrons must be provided from the sample 10. The presence of oxygen in this form on the surface of oxides and non-oxides is well-established and represents the state of the sensor of the invention at time zero (in other words, this is the normal state of the sensor in the presence of only oxygen or air).

The introduction of CO gas into the sensor ambient results in a similar covering of the sensor surface 10a at available sites, as shown in FIG. 1b. Although CO tends to be an electron donating species, i.e., reducing, it may be assumed that the molecule remains neutrally charged on the surface 10a. The rate equation depicting the adsorption of CO is

$$CO(g) \xrightarrow{k_4} CO(ads). \quad (4)$$

In the event that CO and $O^-$ come in close proximity as in FIG. 1c, a reaction between the two may occur, whereby $CO_2$ gas is formed, and an electron is released to the sample 10. This process is shown by Eqn. (5):

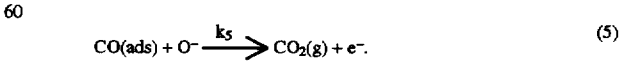

$$CO(ads) + O^- \xrightarrow{k_5} CO_2(g) + e^-. \quad (5)$$

This electron contributes to the overall charge carrier population at the sample surface 10a and therefore the sample resistance. The initial state has an abundance of $O^-$ on the sample surface 10a, making the rate $k_5$ of Eqn. 5 solely dependent upon the concentration of CO adsorbed. One can therefore obtain a value for the relative concentration of CO gas in the ambient by measuring changes in the surface resistance.

Hydrocarbon species are chemisorbed onto the sensor surface 10a as a neutral molecule. The rate equation describing this process is given as $$C_nH_{2m}(g) \xrightarrow{k_6} C_nH_{2m}(ads). \tag{6}$$

When $C_nH_{2m}$ comes in contact with surface adsorbed $O^-$ (via Eqn. 3), a reaction between the two may occur to produce $CO_2$, $H_2O$, and electrons described as $$C_nH_{2m}(ads) + (2n+m)O^- \xrightarrow{k_7} nCO_2(g) + mH_2O + (2n+m)e^-. \tag{7}$$

The number of electrons donated to the sensor surface 10a is therefore particular to the hydrocarbon species in terms of the number of carbon units (n) and the hydrogen saturation (m).

The sensor 12 of the invention is depicted in FIG. 2. A thin film 14 of the metal oxide is formed on a substrate 16. The thickness of the thin film 14 advantageously ranges from about 2,000 Å to 2 μm.

Metal contacts 18a, 18b at two separate points (here, the ends of the film 14) are used to measure the resistance of the thin film. Corresponding leads 20a, 20b provide an output, such as to means 21 for relating the change in surface resistance to the quantity of CO and hydrocarbons. A conventional 4-point probe (not shown) may alternately be employed.

In one embodiment, depicted in FIG. 3, two such sensors 12 are placed in the exhaust pipe 22 of an automobile 24, one prior to the catalytic converter 26, and one after. The leads 20a, 20b are routed to a comparator logic means 28, which compares the two inputs, and sends a signal to the driver by means of a dash warning light 30 if the CO and/or hydrocarbon level from the exhaust exceeds a certain pre-set level. Alternatively, the signal may be used to control the air/fuel mixture in the engine 32, for better combustion efficiency. Such adjustment may be made as the level of CO and/or hydrocarbon increases, for example.

To increase the potential lifetime of the sensor 12 of the invention, a gas sampling scheme has been developed such that the sensor is not continuously exposed to the corrosive environment of the automobile exhaust. Instead, the sensor 12 is located in a separate sampling chamber (not shown) connected to the main exhaust line 22. At regular intervals, a small amount of the exhaust gas is allowed to enter the sensor chamber for sampling and quantitative CO/hydrocarbon determination. Sampling intervals may vary from seconds to minutes, depending on the driving conditions and type of automobile.

Quantitative determination of CO and hydrocarbons is most accurate when the sensor remains isothermal. A small resistance heater embedded in the substrate surface 16 beneath the film 14 in conjunction with a thermocouple (not shown) would increase the thermal stability of the sensor, and thus the detection accuracy.

The thin film sensor of the invention is deposited onto an insulating substrate. The deposition can be accomplished by several conventional thin-film processes, described above, such as sol-gel, MOCVD, or reactive sputtering. In the actual reduction to practice, metal-organic deposition (MOD) was chosen. The starting reagents for this process are metal carboxylate salts dissolved in a common solvent. Examples used in the successful synthesis of high-quality thin-films of $Cu_xMn_{3-x}O_4$, where $0<x\leq 1.5$, were (Cu,Mn)-neodecanoates, (Cu,Mn)-2-ethylhexanoates, and (Cu,Mn)-cyclohexane butyrates. The best results were achieved with Cu-cyclohexane butyrate and Mn-cyclohexane butyrate dissolved in xylene to form a solution with a viscosity between 5 to 10 centipoises. The substrates can be any high temperature, electrically insulating material stable in oxidizing and reducing atmospheres.

In the reduction to practice, polycrystalline $Al_2O_3$ substrates were used with a platinum strip heater screen printed onto the side opposite the deposited film. On the film side of the substrate, platinum electrodes can be screen-printed onto the substrate surface, or it can be left bare with electrode contacts made directly onto the film after deposition. In the reduction to practice, both techniques were used. Deposition of the thin-film had the following sequential steps:

Completely coat the appropriate area of the substrate with the MOD solution;

Spin the substrate at 2,500 to 3,000 rpm for 20 to 30 seconds;

Rapidly heat in air or oxygen to 500° C.—maintain at that temperature for 2 minutes;

Remove sample from heat source and cool to room temperature;

Repeat process to increase film thickness to desired level;

Rapidly heat in air or oxygen to 800° C. for 1 hour;

Remove sample from heat source and cool to room temperature.

Each individual coating deposits a layer between 1,000 to 2,000 Å thick, depending on solution viscosity. A typical film will have between 4 to 10 coatings before the final high temperature treatment at 800° C.

The thin-film sensor of the present invention can operate at temperatures between about 300° to 460° C. The strip heater easily achieves this temperature with input currents between 500 to 800 milliamps. Sensor signals are derived by driving a small constant current through the thin-film sample. The voltage necessary to drive the current is a function of the thin-film resistance. The resistanace of the thin-film is dependent on the concentration of CO and/or HC in the surrounding ambient of the sensor. As the concentration of these gases changes, a correspondingly proportional change in the voltage necessary to drive the constant current is observed. By this method, quantitative evaluation of CO and/or HC levels in the ambient are achieved.

Figure 4:
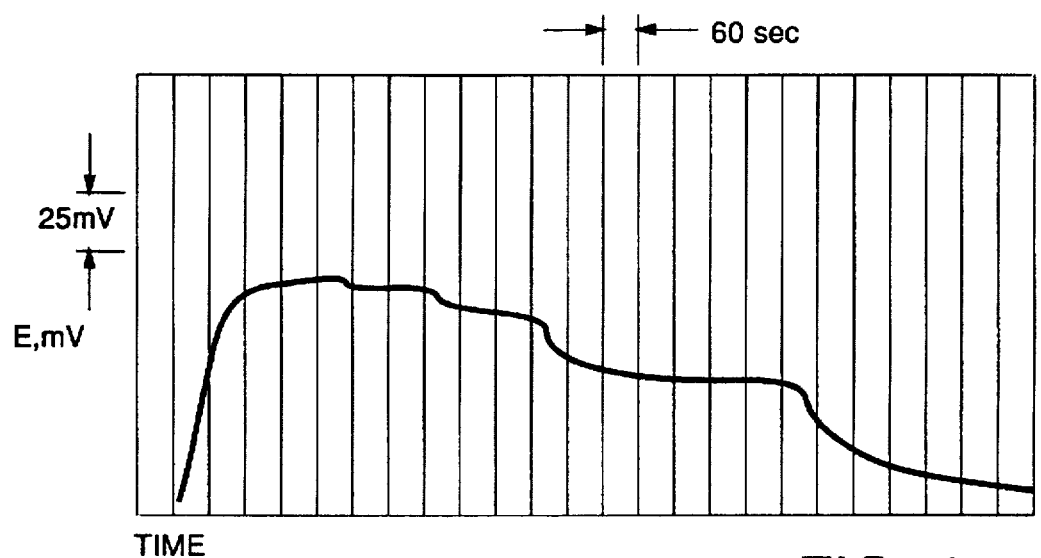
FIG. 4, onto coordinates of potential (in mV) and time, is a plot of signal response of the thin film $CuMn_2O_4$ sensor of the invention at varying CO concentrations in air.
Figure 5:
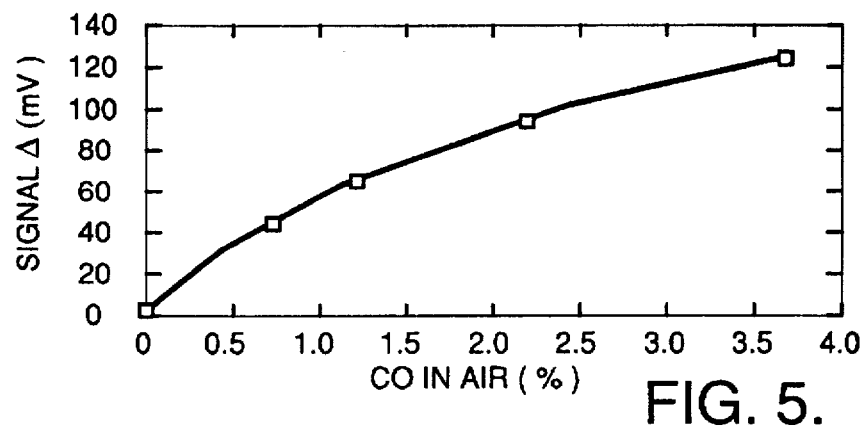
FIG. 5, on coordinates of signal strength (in mV) and CO concentration (% in air) is a calibration plot of the signal strength with concentration of CO in air.

In the reduction to practice, a 5.0 milliamp constant current was driven through the thin-film with the voltage recorded onto a strip chart recorder. The chart recorder output for 3.7, 2.4, and 1.1% CO in air at 460° C. is presented in FIG. 4. An additional data point at 4,600 ppm CO in air is not shown; however, it is included in the calibration plot of signal versus CO concentration shown in FIG. 5.

Figure 6:
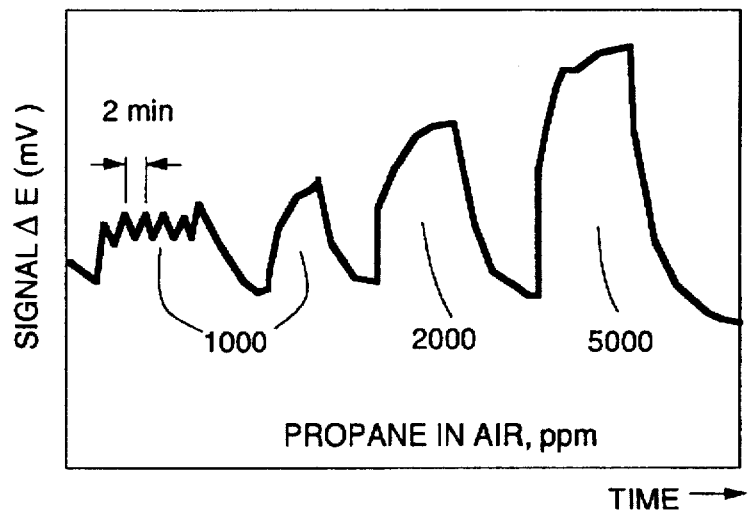
FIG. 6, on coordinates of signal strength (in mV) and time, is a plot of the output from the thin film sensor of the invention for varying propane concentrations in air.
Figure 7:
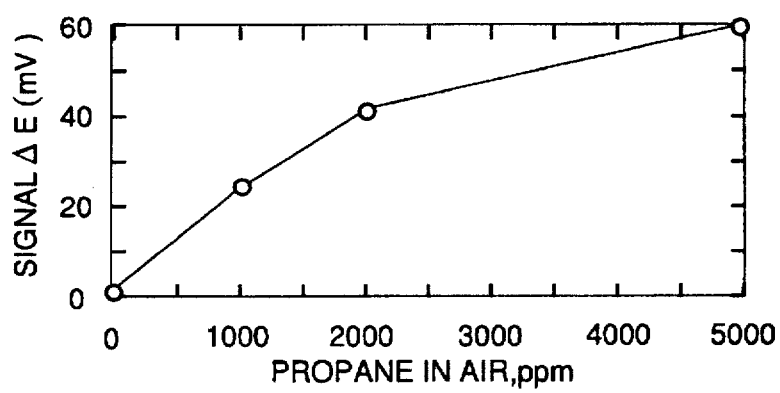
FIG. 7 is a plot similar to that of FIG. 5, but is a calibration plot of the signal strength with concentration of propane in air.
Figure 8:
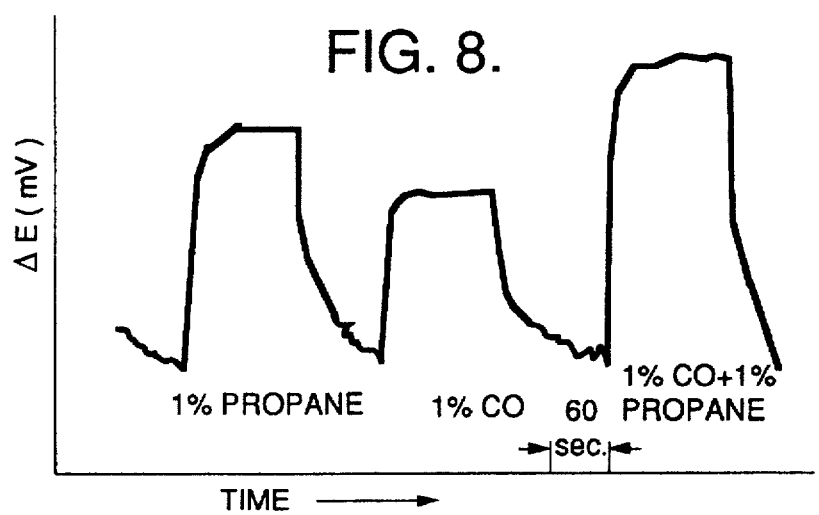
FIG. 8, on coordinates of signal strength (in mV) and time, is a plot showing the additive effect of CO and propane on the signal from the thin film sensor of the invention as a function of time.

Similar chart recorder outputs at 450° C. for the sensor's response to propane in air and a calibration plot are given as FIGS. 6 and 7, respectively. A chart recorder output showing the effect of mixing both CO and propane together in air is presented in FIG. 8. From this data, it is apparent that the two gases have an additive effect on the sensor signal. The combined signal was approximately 16% smaller than the sum of the individual signals, however. This result probably reflects some inaccuracies in the experimental mixing or perhaps some small interference as the gases compete for sites on the sensor. Regardless, the overall additive effect is a main sensor requirement for determining the efficiency of the catalytic converter.

For evaluation of the catalytic converter efficiency, a sensor ideally should be sensitive to both CO and HC such that the presence of either one provides a signal, thereby indicating a conversion inefficiency. The important factor is that the presence of one does not diminish the signal of the other, as is the case when $NO_x$ and CO are present in tin oxide-based measurements. Instead, the signal increases beyond the level achieved by either gas individually (additive), giving an indication of the total CO/HC presence in the exhaust. The fact that the sum of the two gases together is a small percentage less than that which is predicted by their respective individual signals is due to either a precision error in the experimental set-up or an error fundamental to the sensor. In either event, some experimental error is to be expected and does not preclude use of the sensor for determining catalytic converter efficiency once properly calibrated.

It should be noted that the sensor of the present invention is not very sensitive to the presence of methane, which is the least reactive of all the hydrocarbon species in an exhaust stream. Emissions regulations are only concerned with non-methane hydrocarbons, to which the sensor appears to be sensitive. Indeed, propane, which is the hydrocarbon tested herein, is the industry benchmark for HC sensitivity, due to its common occurrence in automobile exhaust.

A properly calibrated pair of sensors could determine catalytic converter efficiency by the following method. Sensor #1 measures a small sample of a specific volume of engine-out exhaust (pre-catalytic converter), while sensor #2 measures another identically sized sample of the same specific volume of gas after it has passed through the catalytic converter. A mass flow sensor (already present on most vehicles) would be incorporated into the sampling scheme to allow the measurement to occur as described.

An alternative method is to measure samples of gas before and after the catalytic converter continuously for specified time period long enough to obtain an average concentration at each measurement point. Comparing the averages would be indicative of the converter efficiency during that time period; for example, 5,000 ppm total average at sensor #1 versus 200 ppm average at sensor #2 would indicate an average efficiency of 96%.

Other data relating to the performance of the thin-film sensors was obtained with bulk samples of $Cu_xMn_{3-x}O_4$, where $0<x\leq1.5$. Bulk-sensors of $Cu_xMn_{3-x}O_4$ were prepared by pressing 1.0 g samples of $Cu_xMn_{3-x}O_4$ powder into pellets with a hydraulic press. A total pressure of $8.8\times10^6$ $N/m^2$ was placed upon a stainless steel die to produce samples 0.625 inch in diameter with a thickness near ⅛ inch before sintering. Samples were subsequently sintered in $Al_2O_3$ boats at 900° C. in air for 18 to 20 hours. The resulting sample pellets were then placed into an evaporator where four gold point-contacts were evaporated onto the surface. Contact layer thicknesses varied between 1 and 2 µm. Gold wires were bonded to the point-contacts at 100° C. using a Kulucke & Soffa model 401U-4 pressure-bonding apparatus. The final product was then heated in air at 750° C. for several hours to anneal out strain in the metal and to promote ohmic contact to the sample.

Figure 9:
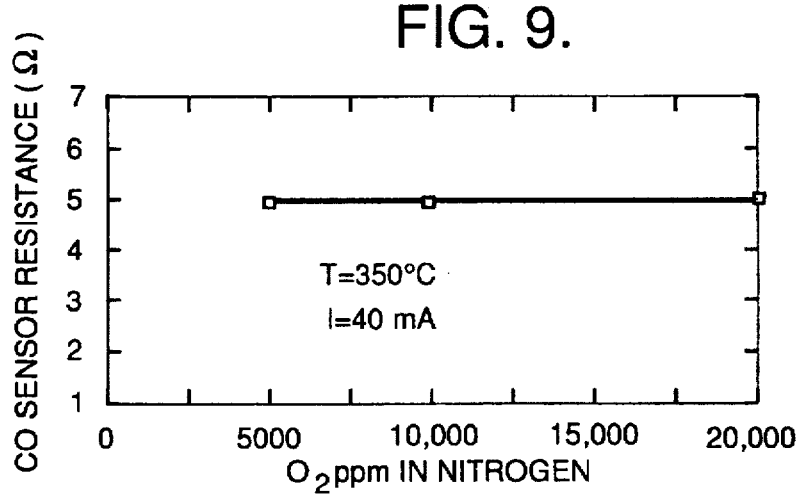
FIG. 9, on coordinates of CO sensor resistance (in ohms) and oxygen concentration (in ppm), is a plot of the bulk sensor signal response to changing oxygen concentration in nitrogen.

Data from these samples are represented in FIGS. 9–11, discussed in greater detail below. The results presented in these Figures are intended to show the advantageous behavior of the $Cu_xMn_{3-x}O_4$ sensor material under various conditions. This behavior is not particular to the form of the material, i.e., bulk or thin film, since both rely on surface changes only. In this connection, however, it will be noted that a 4% CO in air signal is about 120 mV in FIG. 5, while FIG. 11 shows the same concentration giving a signal of 170 µV. This difference is due to the 4-point probe geometry of the bulk samples versus the 2-point measurement for the thin film samples. All the data from the bulk samples will be different in this respect from the thin film data.

FIG. 9 shows that the sensor material, as claimed, does not experience a resistance change from variations in the oxygen partial pressure within the range 5,000 to 20,000 ppm $O_2$.

Furthermore, from FIG. 10, it was determined that the signal from CO was unaffected as the concentration of oxygen in the $CO/O_2$ mixture was varied over a large range. This data has been plotted as the combustion ratio of O:CO, where a signal from 4% CO in nitrogen is shown as the $P(O_2)$ was varied from 0.20 to 0.01 atm. At 0.02 atm, or 2% $O_2$, the stoichiometric ratio for the 4% CO concentration is attained. The sensor signal below this limiting value changes dramatically, as is expected for sensors operating via surface interactions with the ambient gas.

Other data shows the effect of NO gas on the signal response to CO. FIG. 11 plots the bulk sensor signal response to 4% CO in air as the NO gas concentration is increased. As can be seen from the Figure, the signal remains unchanged up to 1% NO addition. Beyond this concentration, the signal decreases slightly. Concentrations of $NO_x$ in exhaust gas is usually in the thousands of ppm range (<1.0%), and should therefore not pose significant interference to the signal from CO.

Figure 12:
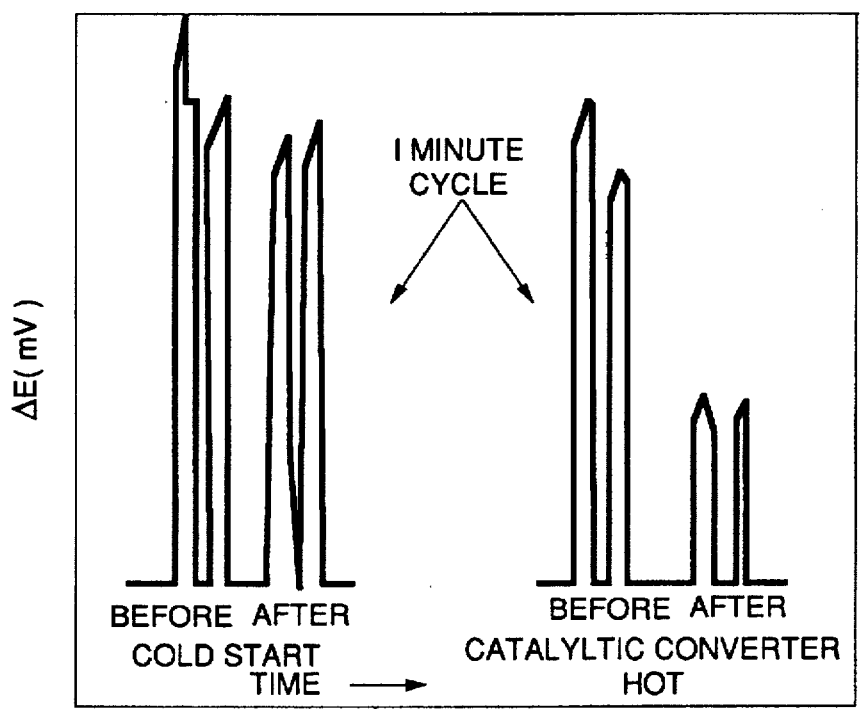
FIG. 12, on coordinates of signal strength (in mV) and time, is a plot of the response of the thin film sensor of the invention to exhaust from before and after a hot/cold catalytic converter for an automobile.

Use of the thin-film sensor as a monitor of the catalytic converter efficiency was also reduced to practice. In these experiments, a test vehicle was modified such that exhaust samples from immediately before and immediately after the catalytic converter could be diverted to the thin-film sensor. Exhaust samples were mixed with a small, unspecified amount of room air to ensure the combustion ratio of O:CO was larger than unity. The results from the sensor using one-minute sampling cycles of the exhaust are presented in FIG. 12. Upon cold start of the vehicle, little difference between the exhaust from before and after the catalytic converter was observed. This result is expected since the catalytic converter was also cold and operating inefficiently, thereby having little effect on the concentration of gases in the tailpipe emissions. After driving the automobile, the sensor response shows a marked decrease in the CO and HC concentrations after the catalytic converter. The concentration before the catalytic converter is for the most part unchanged. These sensor results indicate that the converter was operating with some higher degree of efficiency, as would be expected for higher temperature operation.

Figure 13:
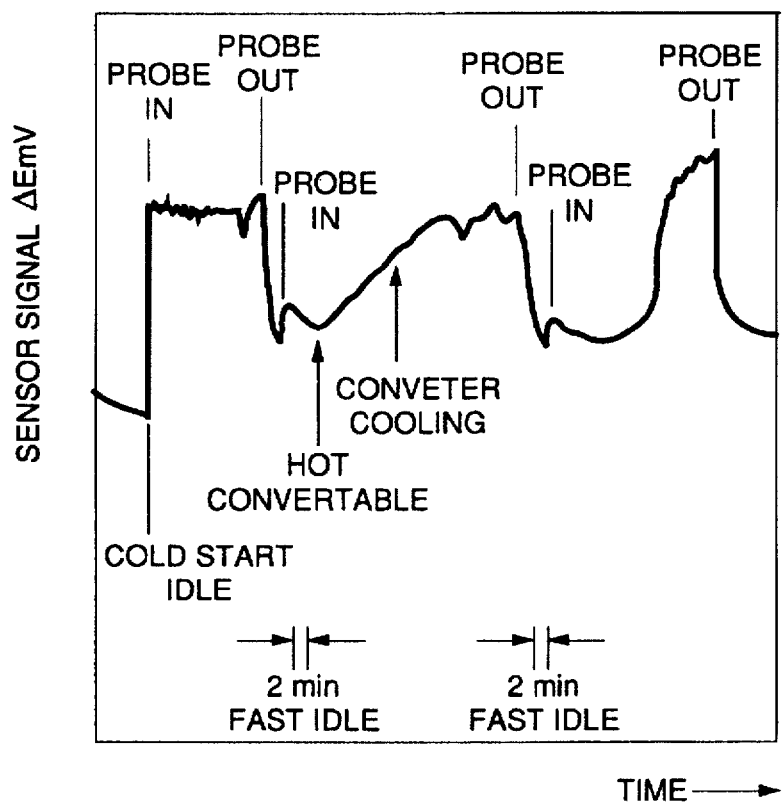
FIG. 13, on coordinates of sensor signal strength (in mv) and time, is a plot of the signal response of the thin film sensor of the invention to tailpipe exhaust of a Dodge truck.

The use of the sensor to observe the effects of the catalytic converter on tailpipe emissions was also demonstrated with a truck. This vehicle was in full compliance with the California emissions regulations. The sensor was placed at the mouth of the tailpipe to examine the CO and HC content of the emanating exhaust. FIG. 13 shows the chart recorder output. The vehicle was initially tested at cold start and left to idle. The corresponding sensor signal reflects the inefficiency of the cold converter. After 12 minutes of idle, the probe was removed from the exhaust stream and the engine was put into a fast idle for two minutes to heat the catalytic converter. Replacing the sensor probe at regular idle yielded a reduced signal indicating an enhanced efficiency for the converter. After several minutes at idle, the converter began to cool and the sensor signal slowly crept up to its original level, indicating a decreased converter efficiency. This sequence was repeated with nearly the identical results, demonstrating the ability of the sensor to track the catalytic converter efficiency.

The advantage of the thin film sensor of the invention over the prior art is twofold. First, potentially interfering gases in automotive exhaust environments, such as $H_2O$ and $NO_x$, do not significantly affect the sensor's signal and sensitivity to CO and HC. Secondly, fluctuations of the $P(O_2)$ also do not affect the signal when the total $P(O_2)$ is greater than the CO and HC combined partial pressures. This requirement is easily achieved in the automobile exhaust since most times the CO and HC levels are in the 1,000 ppm range. Other sensors under consideration, such as $SnO_2$ based sensors, have been found to have signal stability problems in changing $P(O_2)$ environments, as well as extreme signal degradation from $NO_x$.

Thus, there has been disclosed a sensor for detecting CO and hydrocarbons, such as in automobile exhausts. It will be appreciated that various changes and modifications of an obvious nature may be made without departing from the spirit of the invention, and all such changes and modifications are considered to fall within the scope of the invention as defined by the appended claims.

What is claimed is:

1. A thin film sensor for detecting either hydrocarbon gases or a mixture of hydrocarbon and CO gases in a flowing gas steam comprising:
   (a) a thin film comprising $Cu_xMn_{3-x}O_4$, where $0<x<1.5$, said thin film having a resistance which changes as a function of CO and hydrocarbon concentration, said thin film having a surface;
   (b) means for measuring said resistance;
   (c) means for determining any change in free carrier population on said surface of said thin film by determining any difference between a measured quantity of said resistance in the absence of said CO and hydrocarbon gases and a measured quantity of said resistanace in the presence of said flowing gas stream; and
   (d) means for relating the difference to one of hydrocarbon concentration and a mixture of CO and hydrocarbon concentration.

2. The sensor of claim 1 wherein said resistance is determined by measuring the resistance of said surface between at least two separated contact points.

3. The sensor of claim 1 wherein said thin film has a thickness ranging from about 2,000 Å to 2 µm.

4. The sensor of claim 1 for detecting non-methane hydrocarbon gases.

5. A detector system for detecting either hydrocarbon gases or a mixture of hydrocarbon and CO gases in a flowing gas stream comprising:
   (a) two thin film sensors, each comprising
      (1) a thin film comprising $Cu_xMn_{3-x}O_4$, where $0<x<1.5$, said thin film having a resistance which changes as a function of CO and hydrocarbon concentration, said thin film having a surface;
      (2) means for measuring said resistance;
      (3) means for determining any change in free carrier population on said surface of said thin film by determining any difference between a measured quantity of said resistance in the absence of said CO and hydrocarbon gases and a measured quantity of said resistance in the presence of said flowing gas stream; and
      (4) means for relating the difference to one of hydrocarbon concentration and a mixture of CO and hydrocarbon concentration;
   (b) comparator means to compare said resistance of said two thin films and to determine the difference between said two thin film sensors as to concentration of either hydrocarbon gases or a mixture of hydrocarbon and CO gases; and
   (c) output means to provide a warning signal or to make adjustments in engine air/fuel ratio if said difference between said two thin film sensors exceeds a pre-set limit.

6. The detector system of claim 5 wherein each said resistance is determined by measuring the resistance of each said surface between at least two separated contact points.

7. The detector system of claim 5 wherein each said thin film has a thickness ranging from about 2,000 Å to 2 µm.

8. The detector system of claim 5 for detecting non-methane hydrocarbon gases.

9. A method for measuring concentration of either hydrocarbons or a mixture of hydrocarbons and CO in a flowing gas stream comprising:
   (a) causing said gas stream to flow over a thin film surface on a thin film comprising $Cu_xMn_{3-x}O_4$, where $0<x<1.5$, said thin film surface having a resistance which changes as a function of CO and hydrocarbon concentration on said thin film;
   (b) measuring said resistance on said thin film surface;
   (c) determining any difference between a measured quantity of said resistance in the absence of said CO and hydrocarbons and a measured quantity of said resistance in the presence of said flowing gas stream; and
   (d) relating the difference to one of hydrocarbon concentration and a mixture of CO and hydrocarbon concentration.

10. The method of claim 9 wherein said resistance on said thin film surface is determined by measuring the resistance of said thin film surface between at least two separated contact points.

11. The method of claim 9 wherein said thin film has a thickness ranging from about 2,000 Å to 2 µm.

12. The method of claim 9 for measuring concentration of non-methane hydrocarbons.

13. A method for determining efficiency of an automotive catalytic converter comprising measuring concentration of either hydrocarbons or a mixture of hydrocarbons and CO in a flowing gas stream, said method comprising:
   (a) causing said gas stream to flow over a first thin film surface on a first thin film comprising $Cu_xMn_{3-x}O_4$, where $0<x<1.5$, said first thin film surface having a resistance which changes as a function of CO and hydrocarbon concentration on said first thin film, said first thin film surface located prior to said catalytic converter;
   (b) measuring said resistance on said first thin film surface;
   (c) determining any change in said resistance on said first thin film surface by determining any difference between a measured quantity of said resistance in the absence of said CO and hydrocarbons and a measured quantity of said resistance in the presence of said flowing gas stream;
   (d) relating said change in resistance on said first thin film surface to a concentration level of one of hydrocarbons and a mixture of CO and hydrocarbons of said flowing gas stream prior to entry into said catalytic converter;
   (e) causing said gas stream to flow over a second thin film surface on a second thin film comprising $Cu_xMn_{3-x}O_4$, where $0<x<1.5$, said second thin film surface having a resistance which changes as a function of CO and hydrocarbon concentration on said second thin film, said second thin film surface located subsequent to said catalytic converter;
   (f) measuring said resistance on said second thin film surface;

(g) determining any change in said resistance on said second thin film surface by determining any difference between a measured quantity of said resistance in the absence of said CO and hydrocarbons and a measured quantity of said resistance in the presence of said flowing gas stream;

(h) relating said change in resistance on said second thin film surface to a concentration level of one of hydrocarbons and a mixture of CO and hydrocarbons of said flowing gas stream subsequent to egress from said catalytic converter; and (i) comparing said concentration level prior to entry of exhaust gas into said catalytic converter with said concentration level subsequent to egress of exhaust gas from said catalytic converter to thereby determine said efficiency of said catalytic converter.

14. The method of claim 13 wherein said resistance on each said thin film surface is determined by measuring the resistance of each said thin film surface between at least two separated contact points on each respective said thin film surface.

15. The method of claim 13 wherein each said thin film has a thickness ranging from about 2,000 Å to 2 μm.

16. The method of claim 13 for determining efficiency of said automotive catalytic converter comprising measuring concentration of non-methane hydrocarbons.

17. A method for detecting either hydrocarbon gases or a mixture of hydrocarbon and CO gases in a flowing gas stream comprising:

(a) providing first and second thin film sensors, each sensor comprising (1) a thin film comprising $Cu_xMn_{3-x}O_4$, where $0<x<1.5$, said thin film having a resistance which changes as a function of CO and hydrocarbon concentration, said thin film having a surface;

(2) means for measuring said resistance;

(3) means for determining any change in free carrier population on said surface of said thin film from a change in said resistance determined between a measurement made in the absence of said CO and hydrocarbon gases and a measurement made in the presence of said flowing gas stream; and (4) means for relating said change in said resistance to one of hydrocarbon concentration and a mixture of CO and hydrocarbon concentration;

(b) causing said gas stream to flow over said first thin film surface and said second said thin film surface;

(c) measuring said resistance on both said first thin film surface and said second thin film surface;

(d) determining any difference between a measured quantity of said resistance in the absence of said flowing gas stream and a measured quantity of said resistance in the presence of said flowing gas stream;

(e) relating the change in thin film surface resistance to one of hydrocarbon concentration and a mixture of CO and hydrocarbon concentration of said flowing gas;

(f) comparing said resistance of each of said two thin films and determining the difference in concentration of either hydrocarbon gases or a mixture of hydrocarbon and CO gases between said two thin film sensors; and (g) providing a warning signal or making adjustments in engine air/fuel ratio if said difference exceeds a pre-set limit.

18. The method of claim 17 wherein said surface resistance is determined by measuring the resistance of said surface between at least two separated contact points.

19. The method of claim 17 wherein each said thin film has a thickness ranging from about 2,000 Å to 2 μm.

20. The method of claim 17 for detecting non-methane hydrocarbon gases.

* * * * *